US011900556B2

(12) United States Patent
Kosecoff et al.

(10) Patent No.: US 11,900,556 B2
(45) Date of Patent: Feb. 13, 2024

(54) GENERATION OF DIGITAL 3D MODELS OF BODY SURFACES WITH AUTOMATIC FEATURE IDENTIFICATION

(71) Applicant: L'Oreal, Paris (FR)

(72) Inventors: David B. Kosecoff, San Francisco, CA (US); Aldina Suwanto, Clichy (FR); Grégoire Charraud, Levallois-Perret (FR)

(73) Assignee: L'Oreal, Paris (FR)

( * ) Notice: Subject to any disclaimer, the term of this patent is extended or adjusted under 35 U.S.C. 154(b) by 22 days.

(21) Appl. No.: 17/364,704

(22) Filed: Jun. 30, 2021

(65) Prior Publication Data

US 2023/0005229 A1    Jan. 5, 2023

(51) Int. Cl.
*G06T 15/00*    (2011.01)
*G06T 19/20*    (2011.01)
(Continued)

(52) U.S. Cl.
CPC .............. *G06T 19/20* (2013.01); *A61B 5/441* (2013.01); *B29C 64/386* (2017.08); *B33Y 50/00* (2014.12);
(Continued)

(58) Field of Classification Search
CPC ......... G06T 19/00; G06T 17/20; G06T 17/00; G06T 15/10; G06T 15/00
(Continued)

(56) References Cited

U.S. PATENT DOCUMENTS 10,395,099 B2    8/2019  Phamduy et al.
2007/0049832 A1*  3/2007  Edgar ................... H04N 1/628
                                                600/476
(Continued)

FOREIGN PATENT DOCUMENTS

JP    2018117834 A    8/2018
WO   2019/077129 A1   4/2019
(Continued)

OTHER PUBLICATIONS

Written Opinion and Search Report dated Apr. 7, 2022, issued in corresponding French Application No. FR2108971 (French version) filed Aug. 8, 2021, 9 pages.
(Continued)

*Primary Examiner* — Gordon G Liu
(74) *Attorney, Agent, or Firm* — CHRISTENSEN O'CONNOR JOHNSON KINDNESS PLLC

(57) ABSTRACT

A computer system obtains at least one 3D scan of a body surface; automatically identifies, based on the at least one 3D scan, one or more features (e.g., nose, lips, eyes, eyebrows, cheekbones, or specific portions thereof, or other features) of the body surface; and generates a digital 3D model of the body surface. The digital 3D model includes the identified features of the human body surface. In an embodiment, the step of generating of the digital 3D model is based on the at least one 3D scan and the identified features of the body surface. In an embodiment, the digital 3D model comprises a 3D mesh file. The digital 3D model can be used in various ways. For example, output of a manufacturing process (e.g., a 3D printed item, a cosmetics product, a personal care product) can be based on the digital 3D model.

27 Claims, 5 Drawing Sheets

(51) Int. Cl.
| | |
|---|---|
| *G06T 7/579* | (2017.01) |
| *G06T 7/90* | (2017.01) |
| *B29C 64/386* | (2017.01) |
| *A61B 5/00* | (2006.01) |
| *B33Y 50/00* | (2015.01) |
| *G06V 20/64* | (2022.01) |
| *G06V 40/20* | (2022.01) |
| *G06V 40/16* | (2022.01) |

(52) U.S. Cl.
CPC ............... *G06T 7/579* (2017.01); *G06T 7/90* (2017.01); *G06V 20/64* (2022.01); *G06V 40/176* (2022.01); *G06V 40/23* (2022.01); *A61B 5/0077* (2013.01); *G06T 2207/10024* (2013.01); *G06T 2219/012* (2013.01); *G06T 2219/2016* (2013.01); *G06T 2219/2021* (2013.01)

(58) Field of Classification Search
USPC .......................................................... 345/419
See application file for complete search history.

(56) References Cited

U.S. PATENT DOCUMENTS

2012/0038739 A1\* 2/2012 Welch .................. H04N 13/388
 345/426
2015/0366327 A1 12/2015 LaHood, Sr. et al.
2015/0382123 A1 12/2015 Jobani
2016/0217609 A1\* 7/2016 Kornilov ................. G06T 15/60
2020/0337444 A1\* 10/2020 Samain .................. G16H 20/70

FOREIGN PATENT DOCUMENTS

| WO | 2019/077131 A1 | 4/2019 |
|---|---|---|
| WO | 2020/076693 A1 | 4/2020 |

OTHER PUBLICATIONS

Gartenberg, C., "Bellus3D brings its uncanny 3D selfies to the iPhone X", The Verge, <https://www.theverge.com/circuitbreaker/2018/4/11/17226434/bellus3d-face-scanning-iphone-x-app-3d-image-selfie> (Apr. 11, 2018) [retrieved May 13, 2021], 2 pages.

Sony USA, "How to do a selfie scan with 3D Creator", <https://www.sony.com/electronics/support/articles/SX640601> (Oct. 10, 2018) [retrieved May 13, 2021], 6 pages.

Apple Inc., "Scanning and Detecting 3D Objects," <https://developer.apple.com/documentation/arkit/content_anchors/scanning_and_detecting_3d_objects> [retrieved Jun. 30, 2021] (2020), 6 pages.

Apple Inc., "Tracking and Visualizing Faces," <https://developer.apple.com/documentation/arkit/content_anchors/tracking_and_visualizing_faces> [retrieved Jun. 30, 2021] (2020), 6 pages.

\* cited by examiner

GENERATION OF DIGITAL 3D MODELS OF BODY SURFACES WITH AUTOMATIC FEATURE IDENTIFICATION

SUMMARY

In one aspect, the present disclosure is directed to, among other things, a system, including a body feature unit including computational circuitry configured to generate a human body feature digital model responsive to one or more 2-dimensional and 3-dimensional digital representations of the human body feature; an augmented feature unit including computational circuitry configured to modify a sub-feature of the human body feature digital model responsive to one or more feature augmentation inputs and to generate a sub-feature modified digital model of the human body feature; and a reverse-feature unit including computational circuitry configured to generate a reverse-feature digital model of at least a portion of the sub-feature modified model of the human body feature.

In one aspect, the present disclosure is directed to, among other things, a computer system that performs a method comprising obtaining one or more source images including at least one 3-dimensional (3D) scan of a human body surface; automatically identifying, based on the at least one 3D scan, one or more features (e.g., nose, lips, eyes, eyebrows, cheekbones, chin, ears, etc., or specific portions thereof, or other features) of the human body surface; generating a digital 3D model of the human body surface, wherein the digital 3D model includes the identified features of the human body surface; and transmitting the digital 3D model to a manufacturing computer system for use in a manufacturing process such as a 3D printing process. Output of the manufacturing process (e.g., a 3D-printed item, a cosmetics product, a personal care product) is based at least in part on the digital 3D model. In an embodiment, the output of the manufacturing process comprises a 3D-printed physical mold of at least a portion of the human body surface corresponding to the identified feature(s). Further details of the manufacture of such molds can be found, for example, in International Patent Publication Nos. WO2019077131 A1 and WO2019077129 A1, which are incorporated herein by reference.

In an embodiment, the step of generating of the digital 3D model is based on the at least one 3D scan and the identified features of the body surface. In an embodiment, the digital 3D model comprises a 3D mesh file.

In an embodiment, the at least one 3D scan includes multiple depth scans from different angles. Obtaining the 3D scan(s) includes, in an embodiment, checking for visual obstruction of the human body surface during scanning, or checking for and/or adapting the scanning process for changes in facial expression, or other movements or changes in lighting conditions.

In an embodiment, the one or more source images include 2-dimensional (2D) color captures and 3D infrared captures, and generating the digital 3D model of the human body surface includes mapping the 2D color captures to the 3D infrared captures.

In an embodiment, the automatic identification of the identified features includes comparing the 3D scan or one or more other source images against a database of reference images of the identified features. In an embodiment, the automatic identification of the identified features includes determining proximity to or orientation relative to at least one of the identified features to one or more other previously identified features.

In one aspect, the present disclosure is directed to, among other things, a computer system that performs a method comprising obtaining at least one 3D scan of a body surface; automatically identifying, based on the at least one 3D scan of the body surface, a feature of the body surface, including comparing the at least one 3D scan against a database of reference images of the identified feature; and generating a digital 3D model of the body surface, wherein the digital 3D model includes the identified feature.

In an embodiment, the digital 3D model is used in a computer-guided personal care routine, such as a mapping of skin features, administration of a skin treatment, application of a cosmetic product, diagnosis of a skin condition, or tracking changes in skin features over time.

Computer-readable media having stored thereon computer-executable instructions configured to cause a computer system to perform techniques described herein are also disclosed. Corresponding computing devices and systems are also disclosed.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Figure 1:
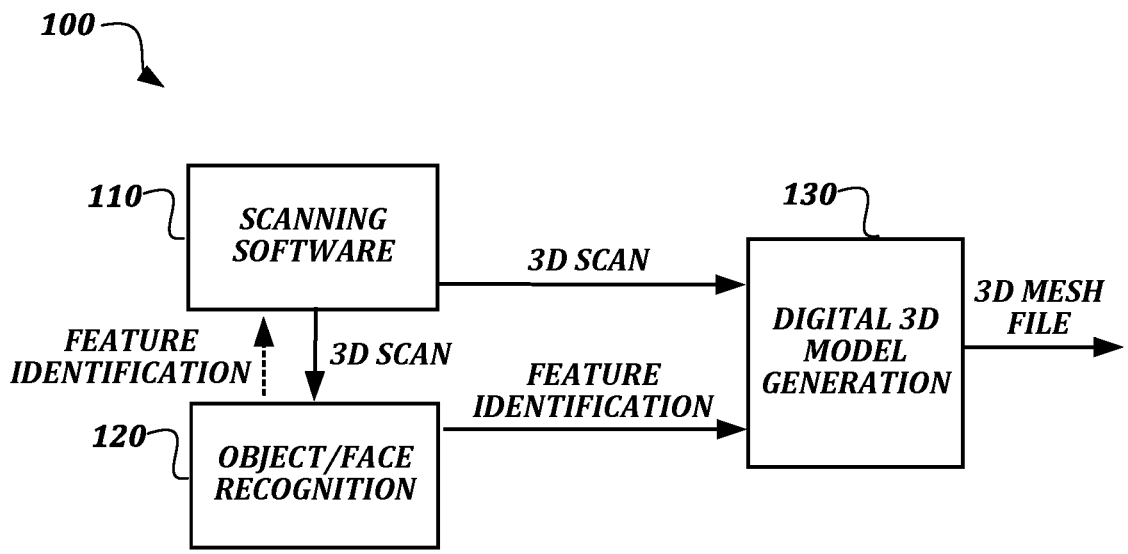
FIG. 1 is a block diagram of a software system for generation of digital 3D models based on 3D scans and automatic feature identification, according to various aspects of the present disclosure.

The foregoing aspects and many of the attendant advantages of the present disclosure will become more readily appreciated as the same become better understood by reference to the following detailed description, when taken in conjunction with the accompanying drawings.

DETAILED DESCRIPTION

Described embodiments include systems and techniques that are useful for obtaining 3-dimensional (3D) scans of features of a live subject, such as scans of the user's own face or a portion thereof, and identifying features (e.g., nose, lips, eyes, eyebrows, cheekbones, chin, ears, etc., or specific portions thereof) in those scans. Such scans and feature identification information can be used in many contexts, including making items such as custom cosmetics, personal care products, or applicators, recommending cosmetics (e.g., colors, tones, or application techniques) to enhance or diminish identified facial features, or diagnosing or tracking skin conditions (e.g. measuring depth of wrinkles, tracking size or geometry of moles or blemishes, depth of pores, etc.).

Described embodiments include a capture phase and a model generation phase. In an illustrative capture phase, a software system obtains one or more source images of a feature or area of interest. The source images include a high-quality 3D scan, which is obtained through, for example, one or more depth scans of a body surface that includes the feature or area of interest. 3D scans are captured in different ways in various embodiments. In an embodiment, scanning software maps 2-dimensional (2D) color captures to 3D monochrome captures of a user in situ. In other embodiments, 3D depth data is captured directly in the IR spectrum (e.g., via IR lasers or IR cameras).

In this regard, sensors suitable for use in described embodiments include 2D cameras, 3D cameras, and depth sensors. Depth sensors are used in an embodiment to obtain 3D information about surfaces and include a range of possible hardware suitable for this purpose, including RGB or infrared stereoscopic cameras, laser or infrared LiDAR sensors, and dot projectors.

In a model generation phase, a software system uses output of the capture phase to produce a digital 3D model of the feature or area of interest that preserves dimensional scale of the feature or area.

In an embodiment, the software system performs feature identification as part of the capture phase and/or model generation phase. In an embodiment, feature identification includes discerning the outline of the targeted feature by comparing the 3D scan against a reference set of relevant images of the same feature in a database using computer vision techniques. In such an embodiment, the reference images represent full views of the corresponding feature or area, either as full 3D scans or as image sets that capture the corresponding feature or area from multiple angles.

In an embodiment, the software system transmits a digital 3D model to a manufacturing computer system for use in manufacturing a product. In an embodiment, the process of generating the digital 3D model is further guided by feature identification information.

In an embodiment, a manufacturing computer system, such as a 3D printing system, uses the digital 3D model to create a custom mold or 3-dimensional stamp of a body surface using a 3D printer or other computer-controlled manufacturing device. As an example, a manufacturing computer system uses a 3D mesh file generated from a 3D scan of a person's face and feature identification information to manufacture a product. In an illustrative scenario, the software system identifies and locates a person's lips in a 3D scan, generates a 3D mesh file based on the date from the 3D scan as well as the feature identification information, and transmits the 3D mesh file to a 3D printing system, which prints a 3D mold or stamp of the user's lips. The mold or stamp helps the person apply lipstick or other cosmetics in a precise manner. As another example, 3D molds of fingernails, eyelids, or other features are created in a similar manner for use in application of cosmetics to corresponding body surfaces.

In an embodiment, feature identification information is used to improve the accuracy of 3D scans while the scans are being performed, which helps to reduce scanning time and/or reduce the likelihood of erroneous data points in the scan. In an embodiment, automated filtering and/or manual touch-up of 3D scans is performed.

In an embodiment, the accuracy of models generated from such scans is improved with feature identification, such as by making adjustments during point-cloud to 3D mesh conversions to remove artifacts that are not consistent with an identified feature. Such techniques reduce the time needed to generate accurate models in an embodiment, such as by reducing the need for manual adjustments after the initial model is generated. In an illustrative scenario, such techniques reduce the time between acquiring the 3D scan and manufacturing a corresponding product, such as by sending a print-ready file to a 3D printing facility to print a 3D element associated with the scanned feature or area. As a result of such techniques, the process of producing a manufactured product is made more accurate and/or efficient.

In an embodiment, machine learning techniques are used to further improve the quality of efficiency of scans or conversions to 3D mesh files. In an embodiment, the number of vector points necessary to accurately reproduce a 3D model are reduced by identifying critical vector points through machine learning algorithms.

FIG. 1 is a block diagram of an illustrative software system for generating digital 3D models based on one or more 3D scans, in accordance with described embodiments. In the example shown in FIG. 1, a software system 100 includes scanning software 110, object/feature identification software 120, and digital 3D model generation software 130. The components of the software system 100 may be implemented in a single computing device or by multiple computing devices working together. Illustrative computing devices, computer systems, and sensors suitable for implementing the software system 100 in various embodiments are described in detail below.

The scanning software 110 obtains at least one 3D scan of a subject. In an embodiment, the 3D scan includes point-cloud data, which is obtained by the scanning software 110. In an embodiment, the scanning software 110 also performs further processing on the 3D scan, such as filtering out erroneous or noisy point-cloud data, before providing the 3D scan to other components of the software system 100.

In the example shown in FIG. 1, the scanning software 110 provides the 3D scan to the object/feature identification software 120. In an embodiment, the object/feature identification software 120 uses face recognition or object recognition techniques, such as those in the ARKit platform available from Apple Inc., to identify features in the 3D scan. In an illustrative scenario, the software identifies a subject's nose, lips, eyes, ears, or other facial features using object recognition techniques.

Described embodiments are capable of implementation in many possible ways to identify features using computer vision techniques, including matching detected edges or contours, color/pixel values, depth information, or the like in different combinations, and at particular threshold levels of confidence, any of which may be adjusted based on lighting conditions, user preferences, system design constraints, or other factors.

In various embodiments, feature identification information is used to improve the accuracy, speed, or efficiency of a completed scan in the capture phase or a subsequently generated digital 3D model in the model generation phase. In an embodiment, feature identification is performed remotely in a cloud computing arrangement, to take advantage of dedicated computing resources for machine learning or artificial intelligence techniques that are impractical to perform in a client computing device.

In an embodiment, the software system 100 optionally performs feature identification during the capture phase, which allows the scanning process to be adapted or a completed scan to be adjusted for more accurate modeling of the identified feature. In an illustrative scenario, the scanning software 110 obtains and sends a first scan to the object/feature identification software 120, which identifies prominent features such a nose, lips, or the like, and feeds this information back (as indicated by the dashed arrow) to the scanning software 110 to guide a subsequent scan, with strategies adapted for scanning particular identified areas. As an example, a scanning process that identifies a nose in a first, low-resolution scan adapts the strategy for a second, higher-resolution scan accordingly. Illustrative information on which adapted scanning strategies can be based include knowledge that a nose has approximate vertical symmetry and that point cloud data in the second scan that is inconsistent with this fact may be adjusted or discarded, or on more specific machine-learning or computer-vision inferences about the geometry of the identified feature or features being scanned.

The scanning software 110 also provides the 3D scan to digital 3D model generation software 130, which generates a digital 3D model. In the example shown in in FIG. 1, the model generation software comprises 3D mesh conversion software, which converts the 3D scan into a 3D mesh file. In an illustrative scenario, the 3D mesh conversion software converts point-cloud data from the 3D scan into a printable 3D mesh file. In an embodiment, the 3D mesh conversion software smooths the meshed contour surface as part of this process.

In an embodiment, the 3D mesh file is an STL file that does not include color or texture information. In other embodiments, where color information is captured during scanning, the software performs color analysis on the scan, e.g., for color-based feature identification or to allow the system to include color information in a resulting 3D model. In still further embodiments, where texture information is captured during scanning, a 3D mesh file with color and/or texture information is generated, such as a VRML file or an OBJ file. Alternatively, the model generation software generates a digital 3D model other than a 3D mesh, such as a solid model.

In an embodiment, the software system 100 is configured to send digital 3D models to a manufacturing system for use in a manufacturing process, such as in 3D printing of stamps or molds as described above, or in production of cosmetics in particular amounts, tints, textures, or the like, based on information in the digital 3D model. As but one example, a digital 3D model of a user's fact may be sent to a custom lipstick manufacturing facility, with tints, textures, or the like being customized based on the model. Alternatively, other uses of digital 3D models are possible that do not involve manufacturing or 3D printing. In an embodiment, a digital 3D model is used to map skin features (e.g., wrinkles, blemishes, visible pores, areas of hyperpigmentation, etc.). Mapping of skin features is useful, for example, to identify changes in skin conditions (e.g., changes in moles, skin pigmentation, skin texture, etc.), which can be helpful in diagnosis of dermatological conditions or for tracking progress of a skin care regimen to improve skin tone, reduce blemishes or acne lesions, minimize the appearance of wrinkles, or for other purposes.

Figure 2A:
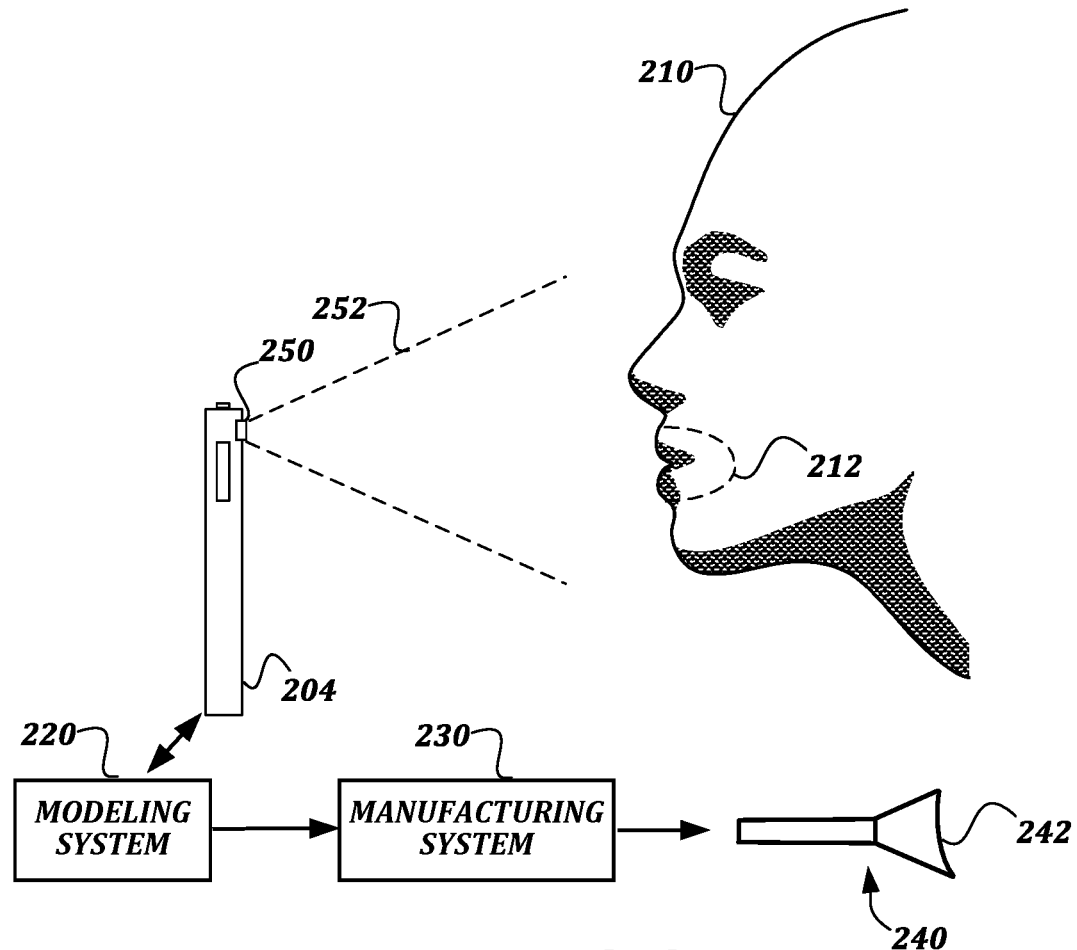
FIG. 2A is a schematic illustration of an arrangement in which a client computing device obtains a 3D scan of a subject and communicates with a modeling system and, optionally, a manufacturing system, according to various aspects of the present disclosure.

FIG. 2A is a schematic illustration of an arrangement in which a client computing device obtains a 3D scan of a subject and communicates with a modeling system and, optionally, a manufacturing system, according to various aspects of the present disclosure. A sensor unit 250 of a client computing device 204 captures image data and/or depth data. In this regard, the sensor unit 250 includes, in an embodiment, one or more cameras (e.g., visible light cameras, IR cameras, etc.), one or more depth sensors, or a combination thereof. In the example shown in FIG. 2A, the client computing device 204 is a mobile computing device such as a smartphone or tablet computer. Alternatively, other client computing devices can be used, such as a laptop or desktop computer, or a dedicated 3D scanning device.

As shown in FIG. 2A, the sensor unit 250 is integrated in the client computing device 204 and is positioned and configured to capture digital representations in the form of, e.g., video or still images, of a region of interest 212 of the subject's face 210 within a field of view 252. Alternatively, the sensor unit 250 is external to the client computing device 204. For example, one or more external 3D scanners or digital cameras in communication with a computing device may be used, or image information is captured in some other way.

Referring to FIG. 2A, in an embodiment, the client computing device communicates with a modeling system 220 configured to generate digital models responsive to one or more 2-dimensional and 3-dimensional digital representations of the human body feature. In an embodiment, the modeling system 220 is implemented in remote computing device separate from the client computing device 204. Alternatively, the modeling system 220 is implemented in whole or in part by the client computing device 204.

Figure 2B:
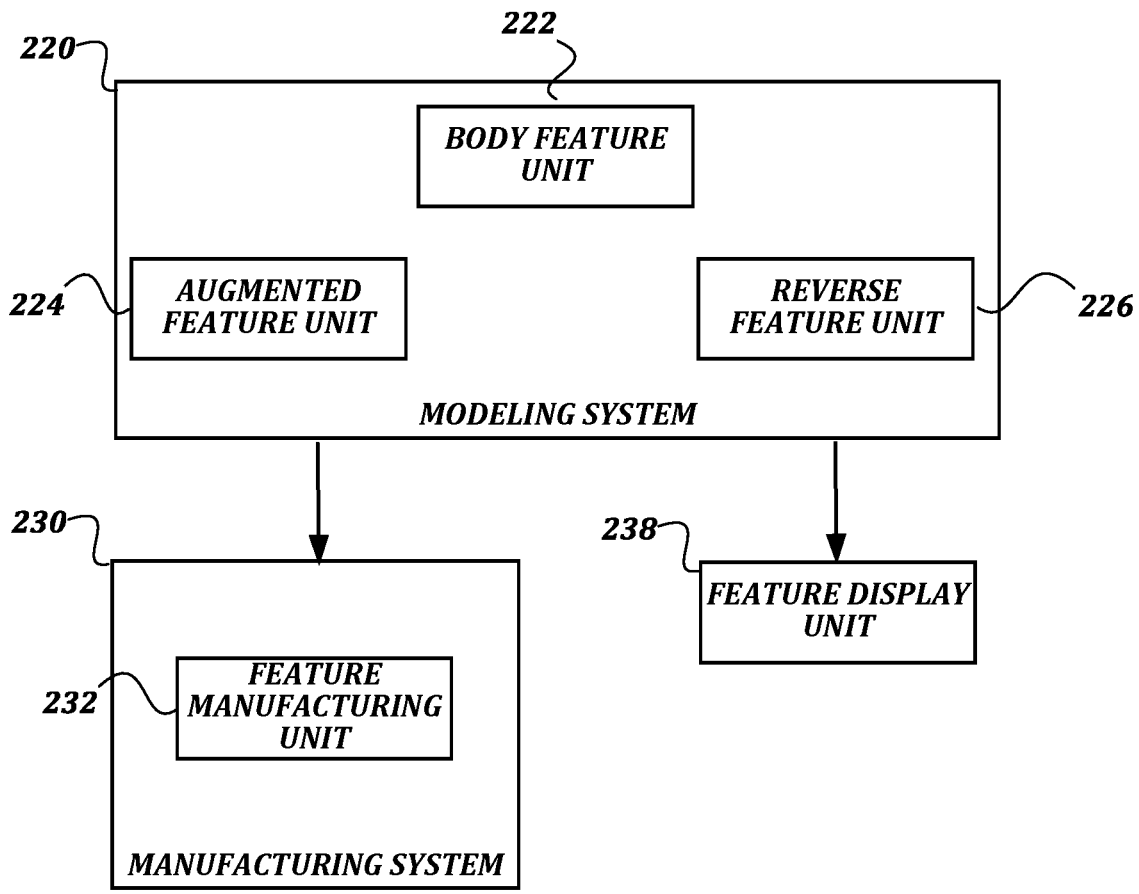
FIG. 2B is a schematic illustration of a modeling system, a manufacturing system, and a feature display unit configured for use in the arrangement of FIG. 2A, according to various aspects of the present disclosure.

Referring to FIG. 2B, in an embodiment, the modeling system 220 includes a body feature unit 222 including computational circuitry configured to generate a human body feature digital model responsive to one or more 2-dimensional and 3-dimensional digital representations of the human body feature and an augmented feature unit 224 including computational circuitry configured to modify a sub-feature of the human body feature digital model responsive to one or more feature augmentation inputs and to generate a sub-feature modified digital model of the human body feature. In an embodiment, the augmented feature unit 224 includes computational circuitry configured to modify a texture, a geometric shape, a surface area, a volume, a pixel dimension, a voxel dimension of the human body feature digital model responsive to one or more feature augmentation inputs and to generate a sub-feature modified model of the human body feature. In an embodiment, the augmented feature unit 224 includes computational circuitry configured to modify the sub-feature of the human body feature digital model responsive to one or more augmentation inputs indicative of a change to a human body feature contour, a change to a human body feature dimension, a change to a human body feature shape, a change to a human body feature surface area, a change to a human body feature surface texture and to generate a sub-feature modified model of the human body feature.

In the example shown in FIG. 2A, the human body feature includes the mouth of the subject, and the sub-feature of the human body feature includes a lip. In an embodiment, the augmented feature unit 224 includes computational circuitry configured to modify the sub-feature of the human body feature digital model responsive to one or more augmentation inputs indicative of a change to a lip contour, a change to a lip dimension, a change to a lip shape, a change to a lip surface area, and/or a change to a lip surface texture, and to generate a sub-feature modified model of the human body feature. In an embodiment, the augmented feature unit 224 includes computational circuitry configured to modify the sub-feature of the human body feature digital model responsive to one or more augmentation inputs indicative of a change to a surface texture, a change to a surface area, a change to a volume, or a change to a geometric dimension. In the example shown in FIG. 2A, the modified sub-feature is a modified lip, with one or more changes in terms of shape, contour, surface area, texture, or the like, relative to the original lip.

Referring again to FIG. 2B, in an embodiment, the modeling system 220 includes a reverse-feature unit 226 including computational circuitry configured to generate a reverse-feature digital model of at least a portion of the sub-feature modified model of the human body feature. In the example shown in FIG. 2A, the reverse-feature digital model includes a concave surface that is a reverse feature of the convex surface of the modified lip. In the example shown in FIG. 2A, the reverse-feature digital model is used to manufacture a custom applicator 242 on a stamp 240 that can be used to apply material, such as lipstick, to a lip, and thereby achieve a desired look or effect that is consistent with the modified sub-feature. The custom applicator 242 has a concave surface that is the reverse of the convex surface of the modified lip.

Referring again to FIG. 2B, in an embodiment, the modeling system 220 communicates with a feature display unit 238 including computational circuitry configured to generate one or more instances of the human body feature digital model, the sub-feature modified digital model of the human body feature, and the reverse-feature digital model for display. In an embodiment, the modeling system 220 communicates with manufacturing system 230, which includes a feature-manufacturing unit 232 including computational circuitry configured to generate an optimized-for-manufacturing digital model of at least one of the human body feature digital model, the sub-feature modified digital model of the human body feature, or the reverse-feature digital model. In the example shown in FIG. 2A, the manufacturing system 230 produces as output the stamp 240, which includes the applicator 242 that has been manufactured according to the reverse-feature digital model.

In an embodiment, the feature-manufacturing unit 238 includes computational circuitry configured to implement a discovery protocol that allows the modeling system 220 and an additive manufacturing apparatus to discover each other, to negotiate one or more pre-shared keys, and to exchange one or more parameters associated with the optimized-for-manufacturing digital model of at least one of the human body feature digital model, the sub-feature modified digital model of the human body feature, or the reverse-feature digital model.

In various embodiments, referring again to FIG. 2A, the sensor unit 250 includes one or more visible light cameras, infrared cameras, or depth sensors, such as LiDAR sensors or TrueDepth cameras available from Apple Inc. In an embodiment, the sensor unit 250 includes multiple cameras, such as for stereoscopic video capture and/or depth sensing. In an embodiment, the sensor unit 250 includes one or more sensors other than cameras (e.g., a LiDAR sensor or infrared dot projector for depth sensing, a proximity sensor, etc.). In an embodiment, an infrared dot projector projects infrared dots onto a surface, and reflections from the surface are measured by an infrared camera to determine the distance each dot is from the projector system. When working in conjunction with a 3D camera, depth measurements can be mapped onto a captured 3D image. This approach is used in an embodiment to generate a 3D model of a body surface.

In an embodiment, the sensor unit 250 remains in a stationary position, while a user turns her head to allow the sensor unit 250 to capture images or video of the body surface 210 from different angles. In other embodiments, the sensor unit 250 is moved manually or automatically to allow the sensor unit 250 to capture images or video of the body surface 210 from different angles while the user's head remains stationary. Scanning software tracks the feature or area of interest as the camera is moved around during the capture process. In an embodiment, the software detects and compensates for changes in the feature or area of interest, such as the user's facial expression or other changes in position or orientation, during the scanning process.

In an embodiment where the sensor unit 250 is moved manually, the user is provided with feedback to guide the user through the scanning process, such by audible or visible cues to guide the user to move her head or the camera in a particular pattern to assist in obtaining accurate scans. In an illustrative scenario, the client computing device 204 provides feedback to a user (e.g., via synthesized voice cues or visual indicators) to adjust the viewing angle of the sensor unit 250 or to follow a particular scanning pattern.

Figure 3:
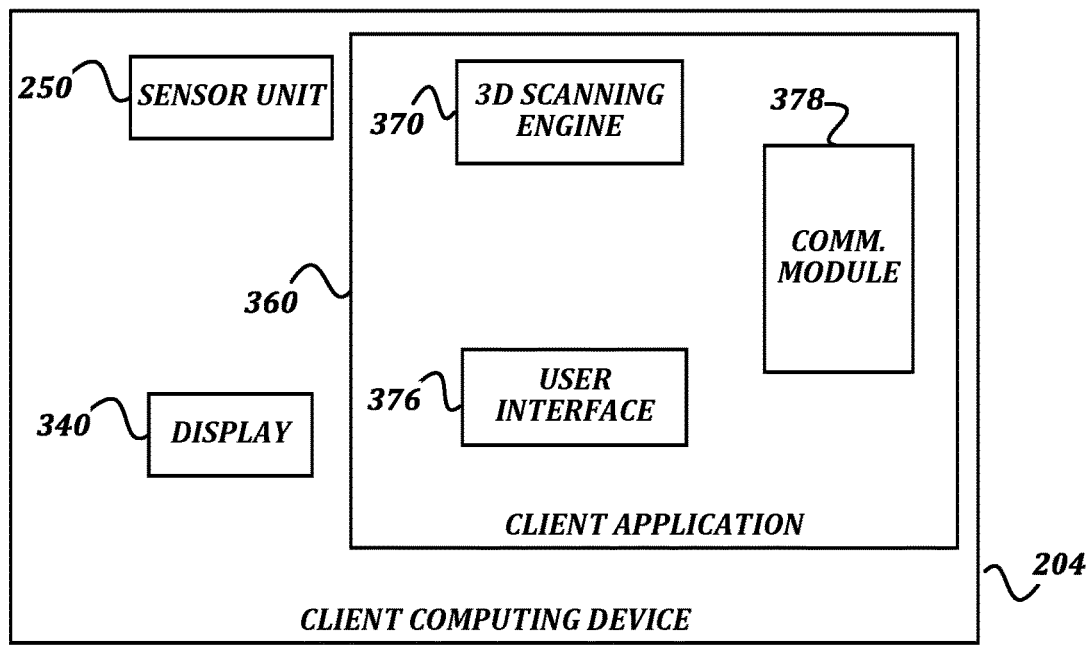
FIG. 3 is a block diagram that illustrates an embodiment of a client computing device according to various aspects of the present disclosure.

FIG. 3 is a block diagram that illustrates an embodiment of a client computing device 204 according to various aspects of the present disclosure. FIG. 3 depicts a non-limiting example of client computing device features and configurations; many other features and configurations are possible within the scope of the present disclosure.

In the example shown in FIG. 3, the client computing device 204 includes a sensor unit 250 and a client application 360. The client application 360 includes a user interface 376. In an embodiment, the user interface 376 includes interactive functionality such as graphical guides to assist a user in positioning the sensor unit 250 correctly, tutorial videos or animations, or other elements. Visual elements of the user interface 376 are presented on a display 340, such as a touchscreen display. In an embodiment, the user interface 376 provides guidance (e.g., visual guides such as arrows or targets, progress indicators, audio/haptic feedback, synthesized speech, etc.) to guide a user to take images under particular lighting conditions, angles, etc., in order to ensure that sufficient data is collected to, e.g., obtain an accurate 3D scan.

In an embodiment, the client application 360 also includes an image capture/3D scanning engine 370 configured to capture and process digital images (e.g., color images, infrared images, depth images, etc.) obtained from camera unit 150. In an embodiment, such images are used to obtain a clean and precise 3D contour mapping of the target body surface (e.g., a face). In an embodiment, the digital images or scans are processed by the client computing device 204 and/or transmitted to a remote computer system for processing in a digital 3D model generation engine or an object/feature identification engine.

In an embodiment, digital 3D models described herein are generated based on sensor data obtained by the client computing device 204. The digital 3D models are generated by the client computing device 204 or by some other computing device, such as a remote cloud computing system, or a combination thereof. In an embodiment, digital 3D models include 3D topology and texture information, which can be used for reproducing an accurate representation of a body surface, such as facial structure and skin features.

A communication module 378 of the client application 360 is used to prepare information for transmission to, or to receive and interpret information from other devices or systems, such as a remote computer system. Such information may include captured digital images, scans, or video, feature identification information, personal care device settings, user preferences, user identifiers, device identifiers, or the like.

Other features of client computing devices are not shown in FIG. 3 for ease of illustration. Alternatively, the client computing device 204 includes different components or circuitry, or the components and circuitry described with reference to FIG. 3 are implemented in some other way. Further description of illustrative computing devices is provided below with reference to FIG. 6.

Figure 4:
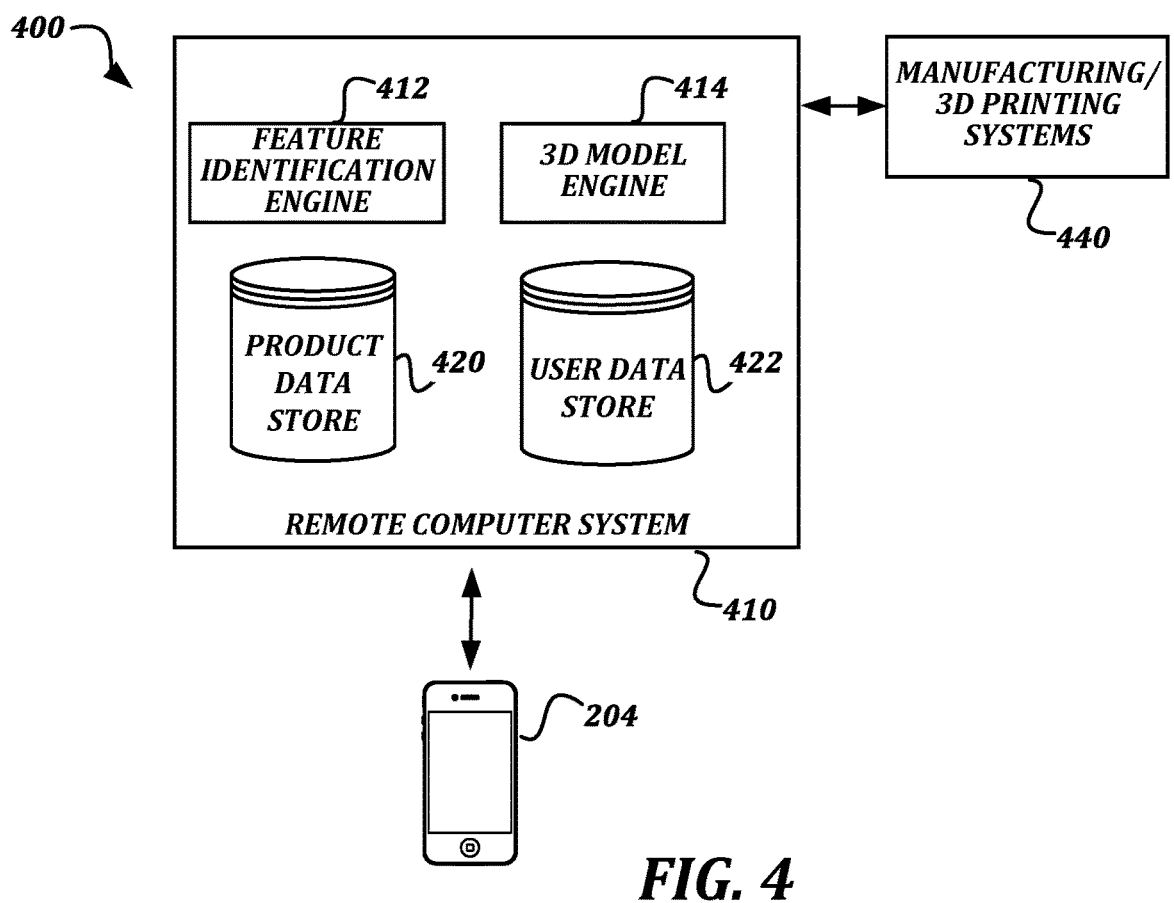
FIG. 4 is a block diagram that illustrates a computer system including a remote computer system, a client computing device, and a manufacturing or 3D printing computer system, in which various aspects of the present disclosure may be implemented.

FIG. 4 is a block diagram that illustrates a system 400 in which various aspects of the present disclosure may be implemented. A client computing device 204 connects to and communicates with a remote computer system 410. In an embodiment, the client computing device 204 captures data representative of body surfaces, such as point cloud data, and transmits this data to the remote computer system 410 for further processing or storage. The client computing device 204 may be used by a consumer, personal care professional, or some other entity to interact with other components of the system 400.

Illustrative components and functionality of the remote computer system 410 will now be described. The remote computer system 410 includes one or more server computers that implement one or more of the illustrated components, e.g., in a cloud computing arrangement. As illustrated in FIG. 4, the components implemented by the remote computer system 410 include a feature identification engine 412, a 3D model generation engine 414, a product data store 420, and a user data store 422.

In an embodiment, the feature identification engine 412 processes data obtained during the capture phase (e.g., point cloud data, color image data, infrared image data, and/or depth data) and generates feature identification information that identifies features of a body surface to be modeled. In an embodiment, the feature identification engine 412 employs machine learning or artificial intelligence techniques (e.g., template matching, feature extraction and matching, classification, artificial neural networks, deep learning architectures, genetic algorithms, or the like) to identify features. For example, the feature identification engine 412 may analyze data obtained during the capture phase such as point cloud data, color data, depth data, or the like to identify facial structures, pigmentation, skin texture, etc., of the user's skin.

In an embodiment, the 3D model generation engine 414 uses feature identification information generated by the feature identification engine 412 and the data obtained during the capture phase to generate a 3D model of a body surface or other object. In an embodiment, data obtained during the capture phase and feature identification information is associated with a user and stored in the user data store 422. In an embodiment, user consent is obtained prior to storing any information that is private to a user or can be used to identify a user.

As explained above, digital 3D models are used in manufacturing or 3D printing systems in an embodiment. Accordingly, the system 400 may include manufacturing/3D printing computer systems 440, which receive digital 3D models from the remote computer system 410 for use in a manufacturing process, such as 3D printing of stamps or molds, production of custom cosmetics, or other processes.

The devices shown in FIGS. 1, 2A, 2B, 3, and 4, or other devices used in described embodiments may communicate with each other via a network (not shown), which may include any suitable communication technology including but not limited to wired technologies such as DSL, Ethernet, fiber optic, USB, and Firewire; wireless technologies such as WiFi, WiMAX, 3G, 4G, LTE, 5G, and Bluetooth; and the Internet. In general, communication between computing devices or components in FIGS. 1, 2A, 2B, 3, and 4, or other components or computing devices used in accordance with described embodiments, occur directly or through intermediate components or devices.

Many alternatives to the arrangements disclosed and described with reference to FIGS. 1, 2A, 2B, 3, and 4 are possible. For example, functionality described as being implemented in multiple components may instead be consolidated into a single component, or functionality described as being implemented in a single component may be implemented in multiple illustrated components, or in other components that are not shown in FIGS. 1, 2A, 2B, 3, and 4. As another example, functionality described as being performed by a particular device may instead be performed by one or more other devices within a system. As an example, the feature identification engine 412 or the 3D model generation engine 414 may be implemented in client computing device 204 or in some other device or combination of devices.

In addition to the technical benefits of described embodiments that are described elsewhere herein, numerous other technical benefits are achieved in an embodiment. For example, the system 400 allows some aspects of the process to be conducted independently by client computing devices, while moving other processing burdens to the remote computer system 410 (which may be a relatively high-powered and reliable computing system), thus improving performance and preserving battery life for functionality provided by client computing devices.

In general, the word "engine," as used herein, refers to logic embodied in hardware or software instructions written in a programming language, such as C, C++, COBOL, JAVA™, PHP, Perl, HTML, CSS, JavaScript, VBScript, ASPX, Microsoft.NET™, and/or the like. An engine may be compiled into executable programs or written in interpreted programming languages. Software engines may be callable from other engines or from themselves. Generally, the engines described herein refer to logical modules that can be merged with other engines or divided into sub-engines. The engines can be stored in any type of computer-readable medium or computer storage device and be stored on and executed by one or more general purpose computers, thus creating a special purpose computer configured to provide the engine or the functionality thereof.

As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, as described further below. One of ordinary skill in the art will recognize that separate data stores described herein may be combined into a single data store, and/or a single data store described herein may be separated into multiple data stores, without departing from the scope of the present disclosure.

Figure 5:
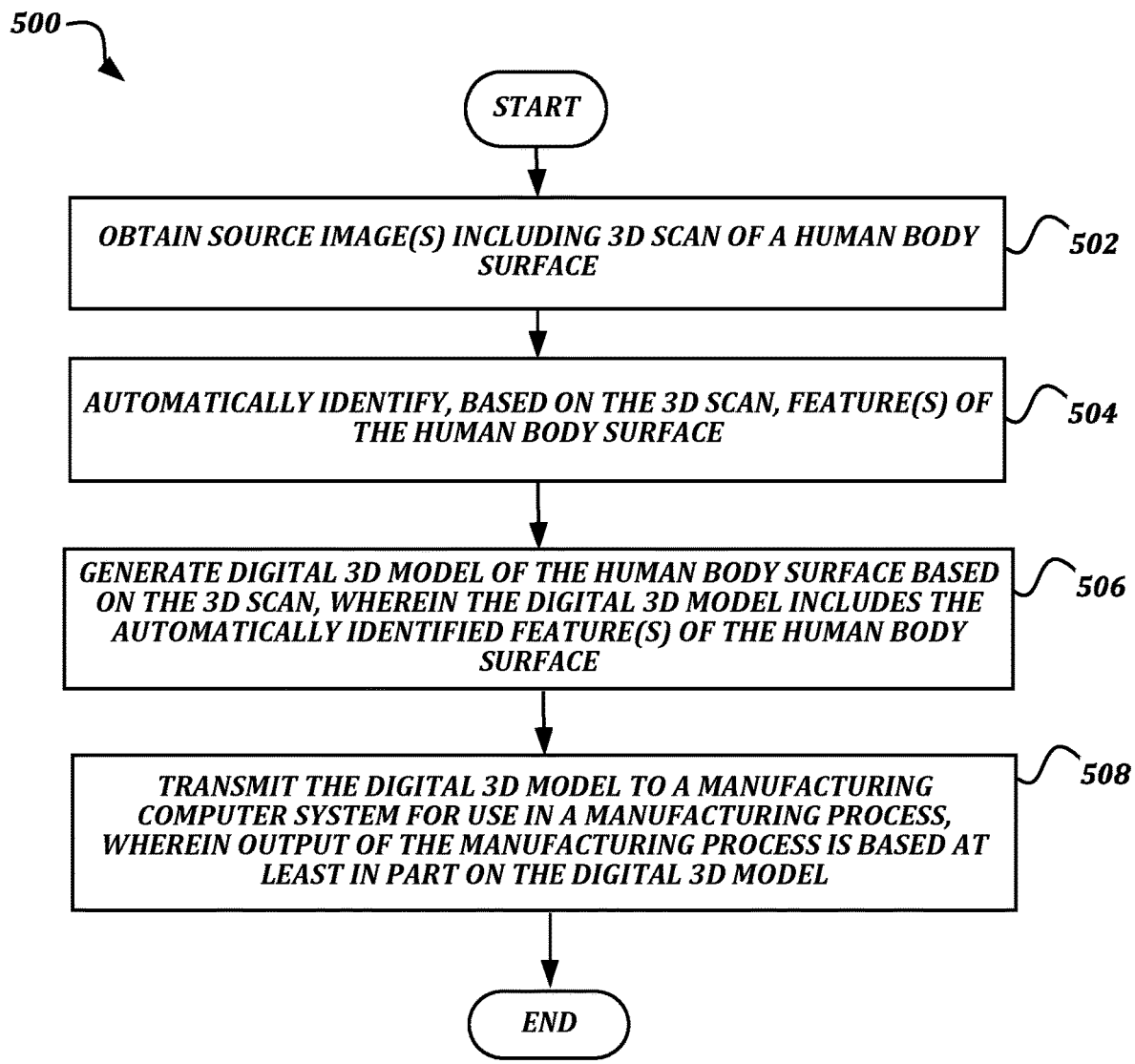
FIG. 5 is a flowchart that illustrates an embodiment of a method of generating and using a digital 3D model, according to various aspects of the present disclosure.

FIG. 5 is a flowchart that illustrates an embodiment of a method of generating and using a digital 3D model of a human body surface, according to various aspects of the present disclosure. The method 500 is performed by a computer system including one or more computing devices, such as remote computer system 410 or some other computing device or combination of devices.

At block 502, a computer system obtains one or more source images, including a 3D scan, of a human body surface, such as a face or other region of interest. In an embodiment, a remote computer system obtains a 3D scan from a client computing device or derives a 3D scan from other source images obtained from a client computing device or some other source. In an embodiment, the computer system obtains multiple depth scans from different angles. In an embodiment, the capture process for the 3D scan includes checking and compensating for changes in facial expression or other movements during scanning. In an embodiment, the capture process for the 3D scan includes checking for obstructions that interfere with scanning of the of the surface. If an obstruction is detected, the scan may be discarded or optionally followed by remedial measures, such as providing feedback to a user to remove the obstruction and restart the scanning process.

At block 504, the computer system automatically identifies one or more features based on the 3D scan. In an embodiment, a remote computer system automatically identifies one or more features in a 3D scan obtained from a client computing device. In an embodiment, the automatic identification of identified features includes determining proximity to and/or directional orientation relative to one or more other previously identified features. In an illustrative scenario, automatic identification of an eyebrow is based at least in part on its proximity to and location above a previously identified eyelid.

At block 506, the computer system generates a digital 3D model of the human body surface based on the 3D scan, in which the automatically identified features are included. In an embodiment, the digital 3D model comprises a 3D mesh file. In an embodiment, the generation of the digital 3D model is further based on feature identification information, as described in other examples herein.

At block 508, the computer system optionally transmits the digital 3D model to a manufacturing or 3D printing computer system, as described above. Alternatively, the digital 3D model is used for some other purpose, as described in other examples herein.

Many alternatives to the process depicted in FIG. 5 are possible, in accordance with embodiments described herein. For example, in an embodiment the process of obtaining a 3D scan is adapted based on identified features, as described above. As another example, techniques and devices described herein are capable of being used to generate models of objects or surfaces other than human body surfaces.

Figure 6:
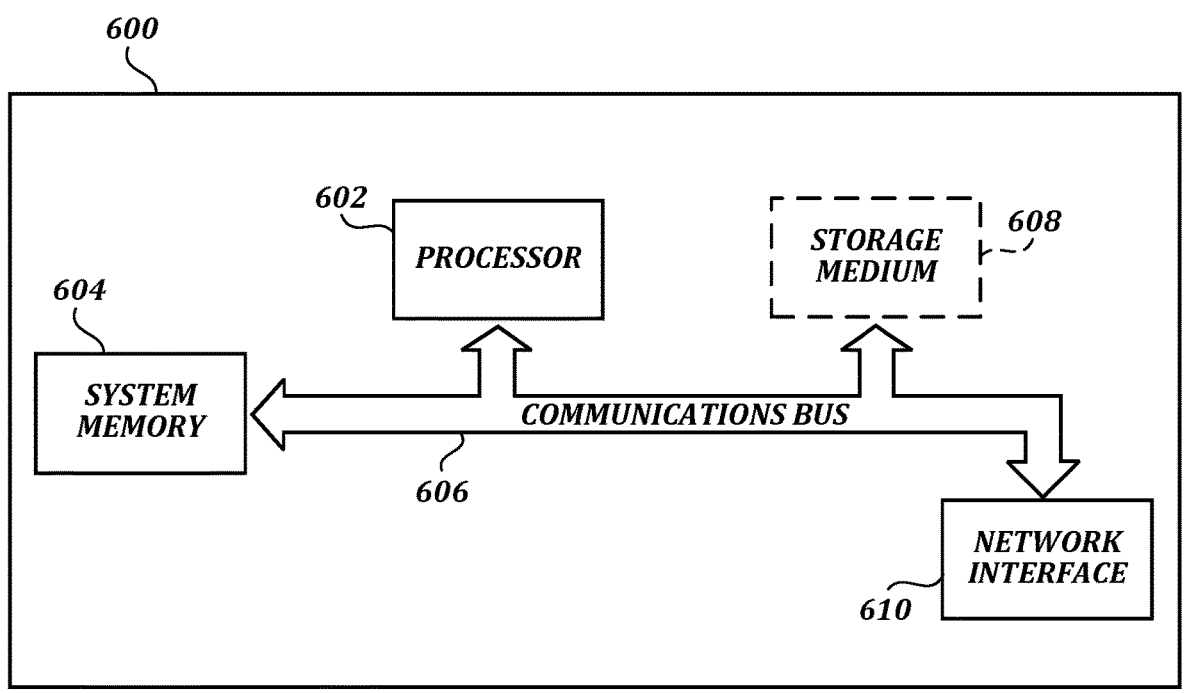
FIG. 6 is a block diagram that illustrates aspects of an illustrative computing device appropriate for use as a computing device of the present disclosure.

FIG. 6 is a block diagram that illustrates aspects of an exemplary computing device 600 appropriate for use as a computing device of the present disclosure. While multiple different types of computing devices were discussed above, the exemplary computing device 600 describes various elements that are common to many different types of computing devices. While FIG. 6 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 600 may be any one of any number of currently available or yet to be developed devices.

In its most basic configuration, the computing device 600 includes at least one processor 602 and a system memory 604 connected by a communication bus 606. Depending on the exact configuration and type of device, the system memory 604 may be volatile or nonvolatile memory, such as read only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 6, the computing device 600 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 610 illustrated in FIG. 6 may represent one or more wireless interfaces or physical communication interfaces.

In the exemplary embodiment depicted in FIG. 6, the computing device 600 also includes a storage medium 608. However, services may be accessed using a computing device that does not include means for persisting data to a local storage medium. Therefore, the storage medium 608 depicted in FIG. 6 is represented with a dashed line to indicate that the storage medium 608 is optional. In any event, the storage medium 608 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 604 and storage medium 608 depicted in FIG. 6 are merely examples of computer-readable media.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 6 does not show some of the typical components of many computing devices. In this regard, the computing device 600 may include input devices, such as a keyboard, keypad, mouse, microphone, touch input device, touch screen, and/or the like. Such input devices may be coupled to the computing device 600 by wired or wireless connections including RF, infrared, serial, parallel, Bluetooth, Bluetooth low energy, USB, or other suitable connections protocols using wireless or physical connections. Similarly, the computing device 600 may also include output devices such as a display, speakers, printer, etc. Since these devices are well known in the art, they are not illustrated or described further herein.

In an embodiment, computational circuitry includes, among other things, one or more computing devices such as a processor (e.g., a microprocessor, a quantum processor, a qubit processor, etc.), a central processing unit (CPU), a digital signal processor (DSP), an application-specific integrated circuit (ASIC), a field programmable gate array (FPGA), and the like, or any combinations thereof, and can include discrete digital or analog circuit elements or electronics, or combinations thereof. In an embodiment, computational circuitry includes one or more ASICs having a plurality of predefined logic components. In an embodiment, computational circuitry includes one or more FPGAs, each having a plurality of programmable logic components.

In an embodiment, computational circuitry includes one or more electric circuits, printed circuits, flexible circuits, electrical conductors, electrodes, cavity resonators, conducting traces, ceramic patterned electrodes, electro-mechanical components, transducers, and the like.

In an embodiment, computational circuitry includes one or more components operably coupled (e.g., communicatively, electromagnetically, magnetically, ultrasonically, optically, inductively, electrically, capacitively coupled, wirelessly coupled, and the like) to each other. In an embodiment, computational circuitry includes one or more remotely located components. In an embodiment, remotely located components are operably coupled, for example, via wireless communication. In an embodiment, remotely located components are operably coupled, for example, via one or more communication modules, receivers, transmitters, transceivers, and the like.

In an embodiment, computational circuitry includes memory that, for example, stores instructions or information. Non-limiting examples of memory include volatile memory (e.g., Random Access Memory (RAM), Dynamic Random Access Memory (DRAM), and the like), non-volatile memory (e.g., Read-Only Memory (ROM), Electrically Erasable Programmable Read-Only Memory (EEPROM), Compact Disc Read-Only Memory (CD-ROM), and the like), persistent memory, and the like. Further non-limiting examples of memory include Erasable Programmable Read-Only Memory (EPROM), flash memory, and the like. In an embodiment, memory is coupled to, for example, one or more computing devices by one or more instructions, information, or power buses.

In an embodiment, computational circuitry includes one or more computer-readable media drives, interface sockets, Universal Serial Bus (USB) ports, memory card slots, and the like, and one or more input/output components such as, for example, a graphical user interface, a display, a keyboard, a keypad, a trackball, a joystick, a touch-screen, a mouse, a switch, a dial, and the like, and any other peripheral device. In an embodiment, computational circuitry includes one or more user input/output components that are operably coupled to at least one computing device configured to control (electrical, electromechanical, software-implemented, firmware-implemented, or other control, or combinations thereof) at least one parameter.

In an embodiment, computational circuitry includes a computer-readable media drive or memory slot that is configured to accept signal-bearing medium (e.g., computer-readable memory media, computer-readable recording media, and the like). In an embodiment, a program for causing a system to execute any of the disclosed methods can be stored on, for example, a computer-readable recording medium, a signal-bearing medium, and the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, and the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, and the like.

In an embodiment, computational circuitry includes acoustic transducers, electroacoustic transducers, electrochemical transducers, electromagnetic transducers, electromechanical transducers, electrostatic transducers, photoelectric transducers, radio-acoustic transducers, thermoelectric transducers, ultrasonic transducers, and the like.

In an embodiment, computational circuitry includes electrical circuitry operably coupled with a transducer (e.g., an actuator, a motor, a piezoelectric crystal, a Micro Electro Mechanical System (MEMS), etc.). In an embodiment, computational circuitry includes electrical circuitry having at least one discrete electrical circuit, electrical circuitry having at least one integrated circuit, or electrical circuitry having at least one application specific integrated circuit. In an embodiment, computational circuitry includes electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method comprising, by a computer system comprising one or more computing devices:
   obtaining one or more source images including at least one 3-dimensional scan of a human body surface;
   automatically identifying, based on the at least one 3-dimensional scan, a feature of the human body surface;
   generating a digital 3-dimensional model of the human body surface, wherein the digital 3-dimensional model includes the identified feature of the human body surface and surface geometry of a sub-feature of the identified feature;

generating a reverse-feature digital model of the digital 3-dimensional model of the human body surface, wherein the reverse-feature digital model includes a surface that is the reverse of the surface geometry of the sub-feature in the digital 3-dimensional model; and transmitting at least one of the digital 3-dimensional model or the reverse-feature digital 3-dimensional model to a manufacturing computer system for use in a manufacturing process, wherein output of the manufacturing process is based at least in part on the digital 3-dimensional model.

2. The method of claim 1, wherein the at least one 3-dimensional scan includes multiple depth scans from different angles.

3. The method of claim 1, wherein the identified feature includes a facial feature.

4. The method of claim 3, wherein obtaining the at least one 3-dimensional scan includes checking for changes in facial expression during scanning.

5. The method of claim 1, wherein obtaining the at least one 3-dimensional scan includes checking for movements of the human body surface during scanning.

6. The method of claim 1, wherein obtaining the at least one 3-dimensional scan includes checking for visual obstruction of the human body surface.

7. The method of claim 1, wherein the one or more source images include 2-dimensional color captures and 3-dimensional infrared captures, and wherein generating the digital 3-dimensional model of the human body surface includes mapping the 2-dimensional color captures to the 3-dimensional infrared captures.

8. The method of claim 1, wherein the automatic identification of the identified feature includes comparing the one or more source images against a database of reference images of the identified feature.

9. The method of claim 1, wherein the automatic identification of the identified feature includes determining proximity to or directional orientation relative to one or more other previously identified features.

10. The method of claim 1, wherein the manufacturing process comprises a 3-dimensional printing process.

11. The method of claim 10, wherein the output of the manufacturing process comprises a 3D-printed physical mold of at least a portion of the human body surface corresponding to the identified feature.

12. The method of claim 1, wherein the output of the manufacturing process includes a cosmetic product or personal care product having a physical characteristic adapted for at least one of the identified feature.

13. The method of claim 1, wherein the generating of the digital 3-dimensional model of the human body surface is based on the at least one 3-dimensional scan and the identified feature of the human body surface.

14. A method comprising, by a computer system comprising one or more computing devices:

obtaining at least one 3-dimensional scan of a body surface at a first resolution;

automatically identifying, based on the at least one 3-dimensional scan of the body surface, a feature of the body surface, including comparing the at least one 3-dimensional scan against a database of reference images of the identified feature;

based on the identified feature, obtaining an additional 3-dimensional scan of the body surface at a second resolution that is higher than the first resolution; and generating a digital 3-dimensional model of the body surface based on the at least one 3-dimensional scan at the first resolution, the additional 3-dimensional scan at the second resolution, and the identified feature of the body surface.

15. The method of claim 14, wherein the identified feature includes a facial feature.

16. The method of claim 14 further comprising using the digital 3-dimensional model in a computer-guided personal care routine.

17. The method of claim 16, wherein the computer-guided personal care routine includes administration of a skin treatment, application of a cosmetic product, or diagnosis of a skin condition.

18. A non-transitory computer-readable medium having stored thereon computer-executable instructions configured to cause a computer system to perform steps comprising:

obtaining at least one 3-dimensional scan of a body surface at a first resolution;

automatically identifying, based on the at least one 3-dimensional scan of the body surface, a feature of the body surface, including comparing the at least one 3-dimensional scan against a database of reference images of the identified feature;

based on the identified feature, obtaining an additional 3-dimensional scan of the body surface at a second resolution that is higher than the first resolution; and generating a digital 3-dimensional model of the body surface based on the at least one 3-dimensional scan at the first resolution, the additional 3-dimensional scan at the second resolution, and the identified feature of the body surface.

19. A computer system comprising one or more computing devices including at least one processor and memory, the memory having stored therein computer-executable instructions configured to cause the computing device to perform steps comprising:

obtaining at least one 3-dimensional scan of a body surface at a first resolution;

automatically identifying, based on the at least one 3-dimensional scan of the body surface, a feature of the body surface, including comparing the at least one 3-dimensional scan against a database of reference images of the identified feature;

based on the identified feature, obtaining an additional 3-dimensional scan of the body surface at a second resolution that is higher than the first resolution; and generating a digital 3-dimensional model of the body surface based on the at least one 3-dimensional scan at the first resolution, the additional 3-dimensional scan at the second resolution, and the identified feature of the body surface.

20. A system, comprising:

a body feature unit including computational circuitry configured to generate a human body feature digital model responsive to one or more 2-dimensional and 3-dimensional digital representations of the human body feature;

an augmented feature unit including computational circuitry configured to modify a sub-feature of the human body feature digital model responsive to one or more feature augmentation inputs and to generate a sub-feature modified digital model of the human body feature including surface geometry of the sub-feature; and a reverse-feature unit including computational circuitry configured to generate a reverse-feature digital model of at least a portion of the sub-feature modified model of the human body feature, wherein the reverse feature digital model includes a surface that is the reverse of the surface geometry of the sub-feature in the sub-feature modified model.

21. The system of claim 20, further comprising:
a feature display unit including computational circuitry configured to generate one or more instances of the human body feature digital model, the sub-feature modified digital model of the human body feature, and the reverse-feature digital model for display.

22. The system of claim 20, further comprising:
a feature-manufacturing unit including computational circuitry configured to generate an optimized for manufacturing digital model of at least one of the human body feature digital model, the sub-feature modified digital model of the human body feature, or the reverse-feature digital model.

23. The system of claim 22, wherein the feature-manufacturing unit includes computational circuitry configured to implement a discovery protocol that allows the system and an additive manufacturing apparatus to discover each other, to negotiate one or more pre-shared keys, and to exchange one or more parameter associated with the optimized for manufacturing digital model of at least one of the human body feature digital model, the sub-feature modified digital model of the human body feature, or the reverse-feature digital model.

24. The system of claim 20, wherein the augmented feature unit includes computational circuitry configured to modify a texture, a geometric shape, a surface area, a volume, a pixel dimension, a voxel dimension of the human body feature digital model responsive to one or more feature augmentation inputs and to generate a sub-feature modified model of the human body feature.

25. The system of claim 20, wherein the augmented feature unit includes computational circuitry configured to modify the sub-feature of the human body feature digital model responsive to one or more augmentation inputs indicative of a change to a human body feature contour, a change to a human body feature dimension, a change to a human body feature shape, a change to a human body feature surface area, a change to a human body feature surface texture and to generate a sub-feature modified model of the human body feature.

26. The system of claim 20, wherein the augmented feature unit includes computational circuitry configured to modify the sub-feature of the human body feature digital model responsive to one or more augmentation inputs indicative of a change to a lip contour, a change to a lip dimension, a change to a lip shape, a change to a lip surface area, a change to a lip surface texture and to generate a sub-feature modified model of the human body feature.

27. The system of claim 20, wherein the augmented feature unit includes computational circuitry configured to modify the sub-feature of the human body feature digital model responsive to one or more augmentation inputs indicative of a change to a surface texture, a change to a surface area, a change to a volume, or a change to a geometric dimension.

* * * * *